US00PP28743P3

(12) United States Plant Patent
van Kleinwee

(10) Patent No.: US PP28,743 P3
(45) Date of Patent: Dec. 5, 2017

(54) *OSTEOSPERMUM* PLANT NAMED 'OSTZ0006'

(50) Latin Name: *Osteospermum ecklonis*
Varietal Denomination: OSTZ0006

(71) Applicant: SYNGENTA PARTICIPATIONS AG, Basel (CH)

(72) Inventor: Theodorus Cornelis Maria van Kleinwee, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 25 days.

(21) Appl. No.: 14/757,250

(22) Filed: Dec. 10, 2015

(65) Prior Publication Data
US 2017/0172044 P1 Jun. 15, 2017

(51) Int. Cl.
*A01H 5/02* (2006.01)

(52) U.S. Cl.
USPC ..... Plt./360

(58) Field of Classification Search
USPC ..... Plt./360
See application file for complete search history.

*Primary Examiner* — Keith O Robinson
(74) *Attorney, Agent, or Firm* — Dale Skalla

(57) ABSTRACT

A new *Osteospermum* plant named 'OSTZ0006' particularly distinguished by the large number of medium sized, white flowers, is freely branching, has medium vigor and is very floriferous throughout the season.

1 Drawing Sheet

Latin name of the genus and species of the plant claimed: *Osteospermum ecklonis.*

Varietal denomination: 'OSTZ0006'.

BACKGROUND OF THE NEW PLANT

The present invention comprises a new and distinct cultivar of *Osteospermum*, botanically known as *Osteospermum ecklonis* (DC.) Norl., and hereinafter referred to by the cultivar name 'OSTZ0006'.

'OSTZ0006' is a product of a planned breeding program. The new cultivar has a large number of medium sized, white flowers, is freely branching, has medium vigor and is very floriferous throughout the season.

'OSTZ0006' originated from an open pollination made in May 2008 in Enkhuizen, The Netherlands. The female parent was an unpatented, proprietary *Osteospermum* plant designated 'M0022-1', having bigger flowers, bigger leaves and a more mounding to trailing plant habit, while plant habit of 'OSTZ0006' is more upright.

As 'OSTZ0006' is the result of an open pollination, the male parent is unknown.

The resulting seeds were sown in January 2009 and 'OSTZ0006' was selected as one flowering plant within the progeny of the stated cross in May 2009 in a controlled environment in Enkhuizen, the Netherlands.

The first act of asexual reproduction of 'OSTZ0006' was accomplished when vegetative cuttings were propagated from the initial selection in the summer of 2009 in a controlled environment in Enkhuizen, The Netherlands.

BRIEF SUMMARY OF THE INVENTION

Horticultural examination of plants grown from cuttings of the plant initiated in the spring of 2010 in Enkhuizen, The Netherlands, and continuing thereafter, has demonstrated that the combination of characteristics as herein disclosed for 'OSTZ0006' are firmly fixed and are retained through successive generations of asexual reproduction. 'OSTZ0006' has not been observed under all possible environmental conditions.

The phenotype may vary significantly with variations in environment such as temperature, light intensity and day length.

A Plant Breeder's Right for this cultivar was not yet applied for.

The following traits have been repeatedly observed and are determined to be basic characteristics of the new variety. The combination of these characteristics distinguishes this *Osteospermum* as a new and distinct variety.

DESCRIPTION OF THE PHOTOGRAPHS

Figure 1:
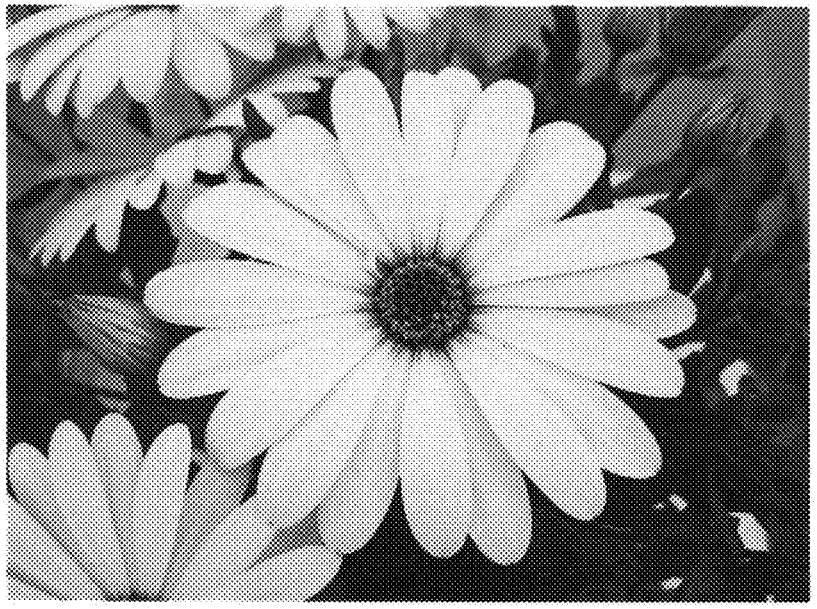
Figure 2:
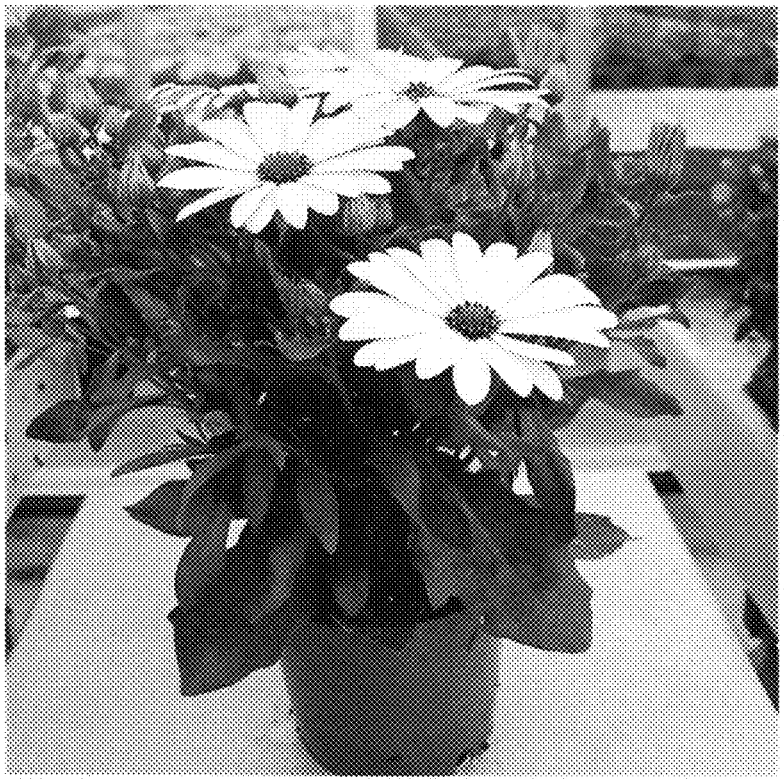

The accompanying photograph drawing shows typical flower and foliage characteristics of 'OSTZ0006' with colors being as true as possible with an illustration of this type. The photograph drawing shows in FIG. 1 a close-up of the flowers, and in FIG. 2 a flowering potted plant of the new variety.

DETAILED BOTANICAL DESCRIPTION

The aforementioned photographs were taken in April 2015 from plants grown in a greenhouse trial in Enkhuizen, The Netherlands. These plants were grown in 10.5 cm pots and were approximately 14 weeks of age. The close-up photograph was taken at the same time.

The observations and measurements were taken in Enkhuizen, The Netherlands, on May 1, 2015, on about 10 week old plants that were growing indoors in 10.5 cm pots. Culture of these plants had started in mid February 2015 with the planting of rooted cuttings.

Color references are made to The Royal Horticultural Society Colour Chart (R.H.S.), 2001.

TABLE 1

DIFFERENCES BETWEEN THE NEW VARIETY 'OSTZ0006' AND A MOST SIMILAR VARIETY

| | 'OSTZ0006' | 'OSTE WHITEYTWO', commercially known as Tradewinds White, U.S. Plant Pat. No.18330 |
|---|---|---|
| Flower shape: | More cup shaped | Flatter |
| Branching habit: | Stronger branching | Fewer branches |
| Floriferousness: | More flowers per plant | Fewer flowers per plant |

Plant:
- *Plant height.*—10 cm.
- *Plant height (inflorescence included).*—17 cm.
- *Plant width.*—25 cm.

Foliage:
- *Arrangement.*—Alternate, simple.
- *Immature leaf, color upper surface.*—RHS 137C.
- *Immature leaf, lower surface.*—RHS 137D.
- *Mature, leaf color, upper surface.*—RHS 147A.
- *Mature leaf, lower surface.*—RHS 147B.
- *Length.*—4.5-8 cm.
- *Width.*—2-5 cm.
- *Shape.*—Cuneate.
- *Base shape.*—Attenuate.
- *Apex shape.*—Obtuse.
- *Margin.*—Crenate with mature leaves, the rest is dentate, medium to deep.
- *Texture, upper surface.*—Very short hair, puberulous.
- *Lower surface.*—Very short hair, dense, canescent, more on veins and edges.
- *Color of veins, upper surface.*—RHS 144B.
- *Color of veins, lower surface.*—RHS 144B.
- *Petiole color.*—RHS 147B-C to RHS 137C.
- *Length.*—1.2 cm.
- *Diameter.*—0.4 cm.
- *Texture.*—Same as leaves.
- *Variegation.*—Absent.

Stem:
- *Quantity of main branches per plant.*—10-12.
- *Color of stem.*—RHS 144B.
- *Length of stem.*—3-8.
- *Diameter.*—0.5-0.8 cm.
- *Length of internodes.*—2-2.5 cm.
- *Texture.*—Glabrous.
- *Color of peduncle.*—RHS 144B.
- *Length of peduncle.*—2-5 cm.
- *Peduncle diameter.*—0.2-0.5 cm.
- *Texture.*—Pubescent.

Inflorescence:
- *Quantity of inflorescences.*—60.
- *Lastingness of individual blooms on the plant.*—10 days.
- *Fragrance.*—None.

Bud (just when opening/showing color):
- *Color.*—RHS 192C turning RHS N144A at the tip.
- *Length.*—2.4 cm.
- *Width.*—1.8 cm.
- *Shape.*—Ovate.
- *Paracorolla.*—Absent.
- *Disk type.*—Daisy.

Immature inflorescence:
- *Diameter.*—5.5 cm.
- *Color of ray florets.*—At the very base RHS N82B, main part white, whiter than RHS155D.

Mature inflorescence:
- *Diameter.*—8-8.5 cm.
- *Diameter of disc.*—1.5 cm.
- *Average quantity of ray florets.*—20.
- *Average quantity of disc florets.*—Approximately 200.

Ray florets:
- *Color upper surface.*—Basal zone: RHS N82B, 0.8 cm, "v" shaped, then whiter than RHS 155D.
- *Color lower surface.*—Longitudinal stripes, RHS 97C and RHS 85D, more purple at the top, more blue at the base. Base edges: RHS 94B.
- *Length.*—4-4.2 cm.
- *Width.*—0.8 cm.
- *Shape.*—Oblanceolate.
- *Apex shape.*—Obtuse.
- *Margin.*—Entire.
- *Texture, upper surface.*—Glabrous.
- *Texture, lower surface.*—Base canescent.

Disc florets:
- *Color of florets.*—RHS 75B+ovary RHS 192C+blue tip: RHS 96C.
- *Length.*—0.8 cm.
- *Width.*—0.3 cm.
- *Shape.*—Tubular, elongated.
- *Apex shape.*—Acute, 5 pointed.
- *Corolla, tube color.*—RHS 75B, with blue tip RHS 96C.
- *Length.*—0.5 cm.
- *Width.*—0.3 cm.
- *Apex shape.*—Acute.
- *Base shape.*—Fused, attached petals — jointed corolla lobs.
- *Margin.*—Entire.
- *Texture.*—Corolla base canescent.

Phyllaries:
- *Quantity.*—About 20.
- *Color, upper surface.*—RHS 146A-B.
- *Color, lower surface.*—RHS 146A-B.
- *Length.*—0.8-1 cm.
- *Width.*—0.2 cm.
- *Shape.*—Ligulate.
- *Apex shape.*—Acute.
- *Base.*—Fused.
- *Margin.*—Entire.
- *Texture.*—Pubescent on lower side, upper side is glabrous.

Reproductive organs:
- *Pistil.*—1.
- *Length.*—0.1 cm.
- *Style color.*—RHS N78C, white at the base RHS 155D.
- *Style length.*—0.1 cm.
- *Stigma color.*—RHS 79A.
- *Stigma shape.*—Roundish.
- *Stamens.*—1.
- *Color of filaments.*—White RHS 155D.
- *Length filaments.*—0.45 cm.
- *Anther color.*—RHS 202A.
- *Color of pollen.*—RHS 21A.
- *Pollen amount.*—Plenty.
- *Resistance to pest and diseases.*—Not observed. Hardiness data are not readily available as the variety has not been tested on frost tolerance.

What is claimed is:

1. A new and distinct variety of *Osteospermum* plant named 'OSTZ0006' substantially as illustrated and described herein.

* * * * *